US00RE50075E

(19) United States
(12) Reissued Patent
Damiano et al.

(10) Patent Number: US RE50,075 E
(45) Date of Reissued Patent: Aug. 13, 2024

(54) GLUCOSE LEVEL CONTROL SYSTEM WITH OFFLINE CONTROL BASED ON PRECEDING PERIODS OF ONLINE CONTROL

(71) Applicant: Trustees of Boston University, Boston, MA (US)

(72) Inventors: Edward R. Damiano, Acton, MA (US); Firas H. El-Khatib, Allston, MA (US)

(73) Assignee: Trustees of Boston University, Boston, MA (US)

(21) Appl. No.: 17/313,401

(22) Filed: May 6, 2021

Related U.S. Patent Documents

Reissue of:

(64) Patent No.: 10,543,313
Issued: Jan. 28, 2020
Appl. No.: 15/221,871
Filed: Jul. 28, 2016

U.S. Applications:

(63) Continuation of application No. PCT/US2015/012861, filed on Jan. 26, 2015.

(Continued)

(51) Int. Cl.
*A61M 5/172* (2006.01)
*A61B 5/00* (2006.01)

(Continued)

(52) U.S. Cl.
CPC ..... *A61M 5/1723* (2013.01); *A61B 5/14532* (2013.01); *A61B 5/4839* (2013.01);

(Continued)

(58) Field of Classification Search
CPC ..... A61M 5/1723
See application file for complete search history.

(56) References Cited

U.S. PATENT DOCUMENTS 4,280,494 A 7/1981 Cosgrove et al.
4,464,170 A 8/1984 Clemens et al.

(Continued)

FOREIGN PATENT DOCUMENTS

CA 2365316 10/2000
CN 1973768 6/2007

(Continued)

OTHER PUBLICATIONS

Albisser et al., May 1974, An Artificial Endocrine Pancreas, Diabetes, 23(5):389-396.

(Continued)

*Primary Examiner* — Cameron Saadat
(74) *Attorney, Agent, or Firm* — BainwoodHuang

(57) ABSTRACT

Apparatus and methods calculate and deliver doses of insulin and optionally glucagon into a subject. Online operation controls delivery of correction doses of insulin automatically in response to regular glucose measurements from a sensor, and offline operation calculates and delivers correction doses based on isolated glucose measurements and information gathered autonomously during preceding online operation. In another aspect, offline operation includes automatically calculating and administering meal doses based on information gathered autonomously during preceding periods of online operation. Both methods include generating relevant control parameters tailored to the individual and continually converged upon and potentially modulated during online operation. The control parameters are employed in real time during periods of offline operation to regulate glucose level (Continued)

without the need for user-provided control parameters such as correction factors and insulin-to-carbohydrate ratios.

40 Claims, 11 Drawing Sheets

Related U.S. Application Data

(60) Provisional application No. 61/933,996, filed on Jan. 31, 2014.

(51) Int. Cl.

| | |
|---|---|
| ***A61B 5/145*** | (2006.01) |
| ***A61M 5/142*** | (2006.01) |
| ***A61M 5/168*** | (2006.01) |
| ***G16H 15/00*** | (2018.01) |
| ***G16H 20/17*** | (2018.01) |

(52) U.S. Cl.

CPC ..... *A61M 5/16827* (2013.01); *G16H 15/00* (2018.01); *G16H 20/17* (2018.01); *A61M 2005/14208* (2013.01); *A61M 2005/14296* (2013.01); *A61M 2202/0486* (2013.01); *A61M 2202/07* (2013.01); *A61M 2205/3584* (2013.01); *A61M 2205/50* (2013.01); *A61M 2205/502* (2013.01); *A61M 2230/005* (2013.01); *A61M 2230/201* (2013.01)

(56) References Cited

U.S. PATENT DOCUMENTS

| | | | |
|---|---|---|---|
| 5,665,065 | A | 9/1997 | Colman |
| 6,544,212 | B2 | 4/2003 | Galley et al. |
| 6,554,798 | B1 | 4/2003 | Mann et al. |
| 6,572,542 | B1 | 6/2003 | Houben |
| 7,347,836 | B2 | 3/2008 | Peterson |
| 7,491,187 | B2 | 2/2009 | Van Den Berghe et al. |
| 7,651,845 | B2 | 1/2010 | Doyle, III et al. |
| 7,655,618 | B2 | 2/2010 | Green et al. |
| 7,678,762 | B2 | 3/2010 | Green et al. |
| 7,678,763 | B2 | 3/2010 | Green et al. |
| 7,683,027 | B2 | 3/2010 | Green et al. |
| 7,766,829 | B2 | 8/2010 | Sloan et al. |
| 7,806,854 | B2 | 10/2010 | Damiano et al. |
| 7,850,641 | B2 | 12/2010 | Lebel et al. |
| 8,185,412 | B1 | 5/2012 | Harpale |
| 8,273,052 | B2 | 9/2012 | Damiano et al. |
| 8,348,842 | B1 | 1/2013 | Osorio |
| 8,377,031 | B2 | 2/2013 | Hayter et al. |
| 8,454,510 | B2 | 6/2013 | Yodfat et al. |
| 8,457,901 | B2 | 6/2013 | Beshan |
| 8,478,557 | B2 | 7/2013 | Hayter |
| 8,562,587 | B2 | 10/2013 | Kovatchev et al. |
| 8,622,988 | B2 | 1/2014 | Hayter |
| 8,679,016 | B2 | 3/2014 | Mastrototaro et al. |
| 8,690,820 | B2 | 4/2014 | Cinar |
| 8,840,582 | B2 | 9/2014 | Blomquist et al. |
| 9,283,323 | B2 | 3/2016 | Toumazou |
| 9,351,670 | B2 | 5/2016 | Dunn |
| 9,398,869 | B2 | 7/2016 | Kovatchev et al. |
| 9,445,757 | B2 | 9/2016 | Desborough |
| 9,486,578 | B2 | 11/2016 | Finan |
| 9,750,438 | B2 | 9/2017 | Kovatchev et al. |
| 9,833,570 | B2 | 12/2017 | El-Khatib et al. |
| 9,839,395 | B2 | 12/2017 | Shariati |
| 9,901,677 | B2 | 2/2018 | Estes |
| 9,907,909 | B2 | 3/2018 | Finan |
| 9,999,728 | B2 | 6/2018 | Parikh |
| 10,188,793 | B2 | 1/2019 | Mazlish |
| 10,188,795 | B2 | 1/2019 | El-Khatib et al. |
| 10,357,607 | B2 | 7/2019 | Blomquist et al. |
| 10,463,786 | B2 | 11/2019 | Saint |
| 10,543,313 | B2 | 1/2020 | Damiano et al. |
| 10,569,016 | B2 | 2/2020 | Rosinko |
| 10,653,834 | B2 | 5/2020 | Kruse et al. |
| 2003/0181852 | A1 | 9/2003 | Mann et al. |
| 2004/0028707 | A1 | 2/2004 | Pinkerton |
| 2004/0034295 | A1 | 2/2004 | Salganicoff |
| 2004/0147872 | A1 | 7/2004 | Thompson |
| 2004/0253736 | A1 | 12/2004 | Stout et al. |
| 2005/0272640 | A1 | 12/2005 | Doyle, III et al. |
| 2006/0272652 | A1* | 12/2006 | Stocker ..... G16H 50/50 128/898 |
| 2006/0276771 | A1 | 12/2006 | Gally |
| 2007/0282299 | A1 | 12/2007 | Hellwig |
| 2008/0154187 | A1 | 6/2008 | Krulevitch |
| 2008/0183060 | A1 | 7/2008 | Steil et al. |
| 2008/0208113 | A1* | 8/2008 | Damiano ..... A61M 5/1723 604/67 |
| 2008/0269714 | A1 | 10/2008 | Mastrototaro |
| 2008/0319384 | A1 | 12/2008 | Yodfat et al. |
| 2009/0006061 | A1 | 1/2009 | Thukral et al. |
| 2009/0164239 | A1 | 6/2009 | Hayter et al. |
| 2009/0177154 | A1 | 7/2009 | Blomquist |
| 2010/0057057 | A1 | 3/2010 | Hayter et al. |
| 2010/0082167 | A1 | 4/2010 | Haueter |
| 2010/0125241 | A1 | 5/2010 | Prud Homme et al. |
| 2010/0137788 | A1 | 6/2010 | Braithwaite et al. |
| 2010/0145262 | A1 | 6/2010 | Bengtsson |
| 2010/0256466 | A1 | 10/2010 | Shekalim |
| 2010/0262117 | A1 | 10/2010 | Magni et al. |
| 2010/0292634 | A1* | 11/2010 | Kircher, Jr. ..... A61B 5/14532 604/66 |
| 2011/0021898 | A1 | 1/2011 | Wei et al. |
| 2011/0054391 | A1 | 3/2011 | Ward et al. |
| 2011/0106049 | A1 | 5/2011 | Damiano et al. |
| 2011/0208155 | A1 | 8/2011 | Palerm et al. |
| 2011/0208156 | A1 | 8/2011 | Doyle, III et al. |
| 2012/0065894 | A1 | 3/2012 | Tubb et al. |
| 2012/0078067 | A1 | 3/2012 | Kovatchev et al. |
| 2012/0245556 | A1 | 9/2012 | Kovatchev et al. |
| 2012/0246106 | A1 | 9/2012 | Atlas et al. |
| 2012/0265126 | A1* | 10/2012 | Estes ..... A61M 5/1413 604/66 |
| 2012/0265722 | A1 | 10/2012 | Blomquist |
| 2012/0277723 | A1 | 11/2012 | Skladnev |
| 2012/0283694 | A1 | 11/2012 | Yodfat et al. |
| 2013/0190583 | A1 | 7/2013 | Grosman |
| 2014/0031786 | A1 | 1/2014 | Kircher, Jr. et al. |
| 2015/0018633 | A1 | 1/2015 | Kovachev et al. |
| 2015/0217052 | A1 | 8/2015 | Keenan et al. |
| 2015/0217053 | A1 | 8/2015 | Booth |
| 2016/0224756 | A1 | 8/2016 | Berger |
| 2016/0331898 | A1 | 11/2016 | Damiano |
| 2017/0095612 | A1 | 4/2017 | El-Khatib et al. |
| 2017/0203038 | A1 | 7/2017 | Desborough et al. |
| 2018/0185587 | A1 | 7/2018 | Brauker |
| 2018/0200440 | A1 | 7/2018 | Mazlish et al. |
| 2019/0214124 | A1 | 7/2019 | Mougiakakou |
| 2019/0247578 | A1 | 8/2019 | Desborough et al. |
| 2019/0336684 | A1 | 11/2019 | O'Connor |
| 2020/0254240 | A1 | 8/2020 | Windmiller |

FOREIGN PATENT DOCUMENTS

| | | | |
|---|---|---|---|
| CN | 201186082 | | 1/2009 |
| CN | 101795623 | | 8/2010 |
| CN | 101821741 | | 9/2010 |
| CN | 102077108 | | 5/2011 |
| CN | 102667787 | | 9/2012 |
| CN | 102802522 | | 11/2012 |
| CN | 102812121 | | 12/2012 |
| CN | 102946923 | | 2/2013 |
| CN | 104667368 | | 8/2017 |
| CN | 104667379 | | 8/2017 |
| EP | 1860583 | A2 | 11/2007 |
| EP | 1 575 656 | | 6/2009 |
| EP | 3 453 414 | | 3/2019 |
| JP | 03-500129 | | 3/1989 |
| JP | 2001-204817 | | 7/2001 |
| JP | 2003-079723 | | 3/2003 |

(56) References Cited

FOREIGN PATENT DOCUMENTS

| | | | |
|---|---|---|---|
| JP | 2004-502474 | | 1/2004 |
| JP | 2007-529241 | | 10/2007 |
| JP | 2007-312923 | | 12/2007 |
| JP | 2012-516735 | | 7/2012 |
| JP | 2012-519018 | | 8/2012 |
| WO | WO 04/006982 | | 1/2004 |
| WO | WO 04/084820 | | 10/2004 |
| WO | WO 06/124716 | | 11/2006 |
| WO | WO 08/057384 | | 5/2008 |
| WO | WO 08/094249 | | 8/2008 |
| WO | WO 08/114254 | | 9/2008 |
| WO | WO 08/157780 | | 12/2008 |
| WO | WO 09/001349 | | 12/2008 |
| WO | 2012/058694 | A2 | 5/2012 |
| WO | WO 12/058694 | | 5/2012 |
| WO | 2012108938 | | 8/2012 |
| WO | WO 14/110541 | | 7/2014 |
| WO | WO 15/021041 | | 2/2015 |

OTHER PUBLICATIONS

Bellazzi et al., 1995, Adaptive Controllers for Intelligent Monitoring, Artif. Intell. Med., 7:515-540.
Bellomo et al., May 1982, Optimal Feedback Glycaemia Regulation in Diabetics, Med. & Biol. Eng. & Comp. 20:329-335.
Berian et al., 2019, A wearable closed-loop insulin delivery systme based on low-power SoCs, Electronics, 8:612.
Botz, May 1976, An Improved Control Algorithm for an Artificial β-Cell, IEEE Trans. Biomed. Eng., BME-23(3):252-255.
Brunetti et al., 1993, A Simulation Study on a Self-Tuning Portable Controller of Blood Glucose, Int. J. Artif. Org., 16(1):51-57.
Candas et al., Feb. 1994, An Adaptive Plasma Glucose Controller Based on a Nonlinear Insulin/Glucose Model, IEEE Trans. Biomed. Eng. 41(2):116-124.
Clemens, 1979, Feedback Control Dynamics for Glucose Controlled Insulin Infusion Systems, Med. Prog. Technol. 6:91-98.
El-Khatib et al., Apr. 14, 2010, A Bihormonal Closed-Loop Artificial Pancreas for Type 1 Diabetes, Science.Trans. Med., 2(27):1-12.
El-Khatib et al., Jul. 2009, A Feasibility Study of Bihormonal Closed-Loop Blood-Glucose Control Using Dual Subcutaneous Infusion of Insulin and Glucagon in Ambulatory Diabetic Swine, Journal of Diabetes Science and Technology, 3(4):789-803.
El-Khatib, et al., Mar. 2007, Adaptive Closed-Loop Control Provides Blood-Glucose Regulation Using Dual Subcutaneous Insulin nd Glucagon Infusion in Diabetic Swine, Journal of Diabetes Science and Technology, 1(2):181-192.
El-Khatib, et al., May 2014, Autonomous and Continuous Adaptation of a Bihormonal Bionic Pancreas in Adults and Adolescents Nilh Type 1 Diabetes, Journal of Clinical Endocrin. Melab., 99(5):1701-1711.
Femat et al., Aug. 22-27, 1999, Blood Glucose Regulation: An Output Feedback Approach, Proc. IEEE Int. Conf. Control App. pp. 1290-1293.
Fischer et al., Aug. 1987, Does Physiological Blood Glucose Control Require an Adaptive Control Strategy?, IEEE Trans. Biomed. Eng., BME-34:575-582.
Fletcher et al., 2001, Feasibility of an Implanted, Closed-Loop, Blood-Glucose Control Device, Immunology 230, Stanford University, Spring 01, 31 pp.
Furler et al., Nov.-Dec. 1985, Blood Glucose Control by Intermittent Loop Closure in the Basal Mode: Computer Simulation Studies with a Diabetic Model, Diabetes Care, 8(6):553-561.
Kan et al., 2000, Novel Control System for Blood Glucose Using a Model Predictive Method, ASAIO Journal, 4:657-662.
Lal et al., Jul. 5, 2019, Realizing a closed-loop (artifical pancreas) system for the treatment of type 1 diabetes, Endocrine reviews, 40(6):1521-1546.
Lauritzen et al., May 1983 Pharmacokinetics of Continuous Subcutaneous Insulin Infusion, Diabetologia, 24(5):326-329.
Marliss et al., Jul. 1977, Normalization of Glycemia in Diabetics During Meals with Insulin and Glucagon Delivery by the Artificial Pancreas, Diabetes, 26:663-672.
Medtronic, 2020, Minimed™ 670G Insulin Pump System, product brochure, https://www.medtronicdiabetes.com/products/minimed-670g-insulin-pump-system, 7 pp.
Pagurek et al., 1972, Adaptive Control of the Human Glucose Regulatory System, Med. Biol. Eng., 10:752-761.
Panteleon et al., Jul. 2006, Evaluation of the effect of gain on the meal response of an automated closed-loop insulin delivery system, Diabetes, 55:1995-2000.
Parker et al., 1996, Model Predictive Control for Infusion Pump Insulin Delivery, Proceedings of the 18th Annual International Conference of the IEEE, 6:1822-1823.
Parker et al., Feb. 1999, A Model-Based Algorithm for Blood Glucose Control in Type I Diabetic Patients, IEEE Trans. Biomed. Eng. 46(2):148-157.
Parker et al., Jan.-Feb. 2001, The Intravenous Route to Blood Glucose Control, IEEE Eng. Med. & Biol., pp. 65-73.
Parrish et al., Jun. 1997, Control of an Artificial Human Pancreas Using the SDRE Method, Proc. American Control Conf., 2:1059-1060.
Russell et al., Nov. 2010, Efficacy Determinants of Subcutaneous Microdose Glucagon during Closed-Loop Control, Journal of Diabetes Science and Technology, 4(6):1288-1304.
Russell, et al., Jun. 15, 2014, Outpatient Glycemic Control with a Bionic Pancreas in Type 1 Diabetes, The New England Journal of Medicine, 371(4):313-325.
Russell, et al., Nov. 2012, Blood Glucose Control in Type 1 Diabetes With a Bihormonal Bionic Endocrine Pancreas, Diabetes Care, 35:2148-2155.
Sivaramakrishnan et al., 2017, Optimal model based control for blood glucose insulin system using continuous glucose monitoring, J. Pharm. Sci & Res., 9(4):465-469.
Steil et al., 2006, Metabolic modelling and the closed-loop insulin delivery problem, Diabetes Research and Clinical Practice, 74:S183-S186.
Steil et al., Dec. 2006, Feasibility of automating insulin delivery for the treatment of type 1 diabetes, Diabetes, 55:3344-3350.
Trajanoski et al., Sep. 1998, Neural Predictive Controller for Insulin Delivery Using the Subcutaneous Route, Biomedical Engineering, 45(9):1122-1134.

* cited by examiner

GLUCOSE LEVEL CONTROL SYSTEM WITH OFFLINE CONTROL BASED ON PRECEDING PERIODS OF ONLINE CONTROL

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

STATEMENT OF U.S. GOVERNMENT RIGHTS

The invention was made with Government support under Contract No. DK085633 awarded by the National Institutes of Health. The Government has certain rights in the invention.

BACKGROUND

Standard-of-care insulin therapies for regulating blood glucose in diabetes typically involve either multiple daily subcutaneous injections or subcutaneous infusion with an insulin pump. Typically, combinations of basal and bolus insulin are administered to meet the subject's basal metabolic insulin requirement; correction bolus doses are administered to regulate hyperglycemia; and additional meal bolus doses are added to provide insulin for food consumption. In current usual care, a correction bolus of insulin that is typically administered to treat a hyperglycemic state is based on an estimate of the individual's so-called "correction factor(s)", which relate how much insulin is estimated by the user to adequately compensate for different levels of hyperglycemia. Correction factors are heuristically estimated on an individual basis and are modified (essentially by trial-and-error) from time to time. This is similar to how basal rates of insulin are heuristically estimated on an individual basis to provide basal metabolic insulin requirements.

Similarly, meal bolus insulin doses taken around food consumption are also typically estimated heuristically on an individual basis based on the quantity and content (carbohydrate and other) of the food, in conjunction with a heuristic estimate of the individual's so-called "insulin-to-carbohydrate ratio(s)", among other factors such as the time of the day, physical activity, health state, emotional state, etc. The right correction bolus doses, insulin basal rates, and meal bolus doses alike, are all essentially determined by trial-and-error experience and could vary significantly among individuals as well as for an individual over time; yet, they are all critical determinants of how well an individual is able to control their blood glucose. Dosing requirements are also subject to factors such as the time of the day, physical activity, health state, emotional state, etc., and could vary over periods of hours, days, or weeks due to transient changes (e.g. due to circadian hormonal fluctuations, current illness, physical activity, or emotional state) and/or periods of months or years due to developmental changes (e.g. due to hormonal changes that occur during puberty or menopause).

SUMMARY

Disclosed herein are automated methods for calculating and delivering doses of insulin or insulin-like agents and/or a counter-regulatory agent such as glucagon or glucagon-like agents, infused into a subject via any of several routes including subcutaneously, intramuscularly, intraperitoneally, or intravenously. The methods adapt to an individual user and do not require inputs such as "correction factors" and "insulin-to-carbohydrate" factors.

A first disclosed method includes periods of online operation when a controller is operating to control the delivery of correction boluses of insulin automatically in response to regular glucose levels provided by a sensor at regular intervals (e.g., on the order of 1-15 minutes apart), also referred to as "sampling intervals". Online operation of the controller refers to sampling intervals when there are a glucose measurements provided by the sensor and offline operation refers to sampling intervals when there are no glucose measurements provided by the sensor. The method further includes offline operation when a controller responds automatically to isolated glucose measurements (e.g., provided by the subject to the controller), using information that was gathered autonomously by the control system during preceding periods of online operation. A second disclosed method includes automatically calculating and administering meal bolus doses in response to meal announcements during periods of offline operation based on information that was gathered autonomously by the control system during preceding periods of online operation. The two methods involve autonomously generating relevant control parameters that are tailored to the individual and are continually converged upon and potentially modulated during periods of online operation. The control parameters are then employed in real time during periods of offline operation in order to regulate glucose levels without the need for the user to provide corresponding control parameters (e.g. insulin-to-carbohydrate ratios, or insulin correction factors). The methods may be used independently or together, and they may also be supplemented by analogous control methods for delivery of a counter-regulatory agent during offline operation, as described more below.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views.

DETAILED DESCRIPTION

The disclosures of the following published patent documents are incorporated by reference herein:

US patent publication 2008/0208113 A1

PCT application publication WO 2012/058694 A2

US patent application publication 20130245547 A1

Figure 1:
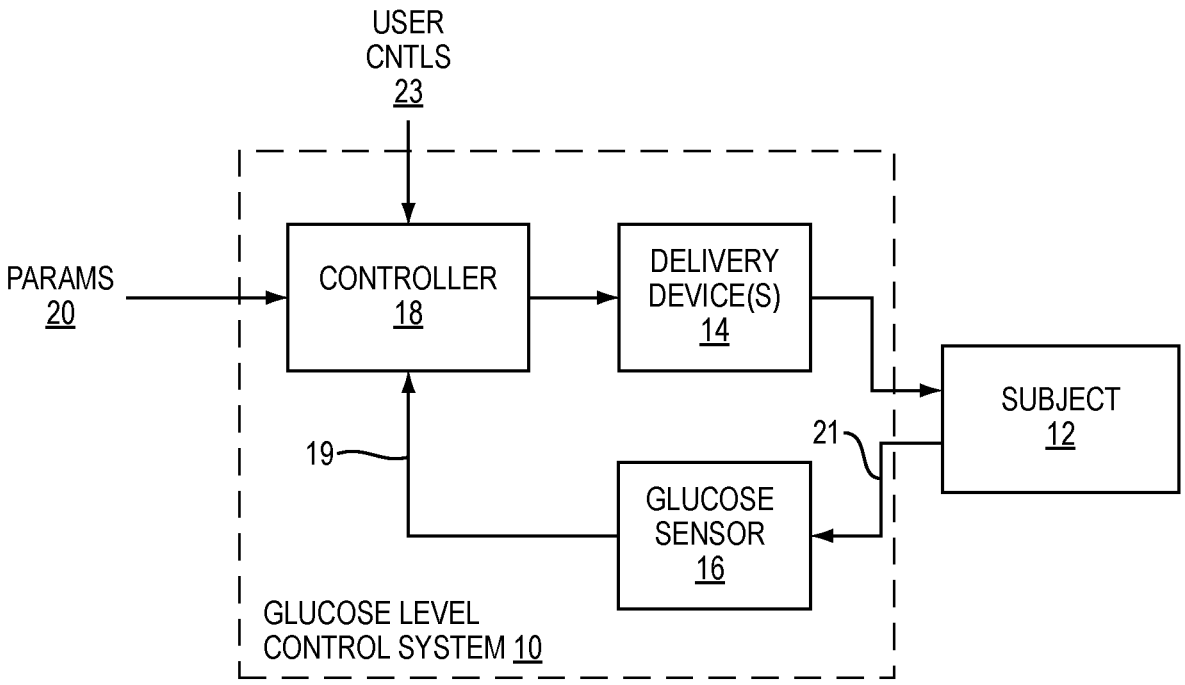
FIG. 1 is a block diagram of a glucose control system.

FIG. 1 illustrates an automated control system 10 for regulating the glucose level of an animal subject (subject) 12, which may be a human. The subject 12 receives doses of insulin from one or more delivery devices 14, for example infusion pump(s) coupled by catheter(s) to a subcutaneous space of the subject 12. As described below, the delivery devices 14 may also deliver a counter-regulatory agent such as glucagon for control of glucose level under certain circumstances. For the delivery of both insulin and glucagon, the delivery devices 14 are preferably mechanically driven infusion mechanisms having dual cartridges for insulin and glucagon respectively. In the present description, reference is made to glucagon specifically, but it is to be understood that this is for convenience only and that other counter-regulatory agents may be used. Similarly, the term "insulin" herein is to be understood as encompassing all forms of insulin-like substances including natural human or animal insulin as well as synthetic insulin in any of a variety of forms (commonly referred to as "insulin analogs").

For online or autonomous operation, a glucose sensor 16 is operatively coupled to the subject 12 to continually sample a glucose level of the subject 12. Sensing may be accomplished in a variety of ways, generally involving some form of physical coupling 21 between the subject 12 and the glucose sensor 16. A controller 18 controls operation of the delivery device(s) 14 as a function of a glucose level signal 19 from the glucose sensor 16 and subject to programmed input parameters (PARAMS) 20 which may be provided by a user such as the subject 12. One input parameter for automatic operation is the weight of the subject 12. One feature of the disclosed technique is its ability to provide effective automated control without receiving explicit information regarding either meals that the subject 12 has ingested or any other "feedforward" information, which is achieved in part by an adaptive aspect to operation of the controller 18.

The controller 18 is an electrical device with control circuitry that provides operating functionality as described herein. In one embodiment, the controller 18 may be realized as a computerized device having computer instruction processing circuitry that executes one or more computer programs each including respective sets of computer instructions. In this case the processing circuitry will generally include one or more processors along with memory and input/output circuitry coupled to the processor(s), where the memory stores computer program instructions and data and the input/output circuitry provides interface(s) to external devices such as the glucose sensor 16 and delivery device(s) 14.

The control system 10 is also able to operate in an offline manner in which it is used to provide delivery of insulin (and potentially glucagon as well) but not based on glucose levels reported by the sensor 16. Thus, overall operation may be divided between online periods each including a succession of sampling intervals when a glucose signal (level) 19 is available, and offline periods each including a succession of sampling intervals when the glucose signal (level) 19 is either completely or only intermittently unavailable. The description below uses the terms "online" and "offline" for these periods. Also, offline operation may be user-selected for some reason even when a glucose level signal 19 is available for use.

User control inputs (USER CNTLs 23) may be provided via a local or remote user interface of some type. In one embodiment, the user interface may resemble that of conventional insulin pumps or similar devices, e.g., by including control buttons for commanding the delivery of a bolus and perhaps a small display. In other embodiments, the system may have a wired or wireless interface to a remote device that may incorporate a fuller-function user interface, such as a smartphone or analogous personal computing device. In offline mode, the glucose sensor 16 may be absent, non-functioning, or not coupled to the subject 12, with the result that the blood glucose signal 19 is not available to control automatic operation.

The description herein refers to a "user" as the source of the user control inputs 23. In one typical use, the glucose level control system 10 is a personal device worn by a subject 12 for continual glucose control. In this case the user and subject 12 are the same person. In other uses, there may be another person involved in the care of the subject 12 and providing control input, and in such a case that other person has the role of user.

Figure 2:
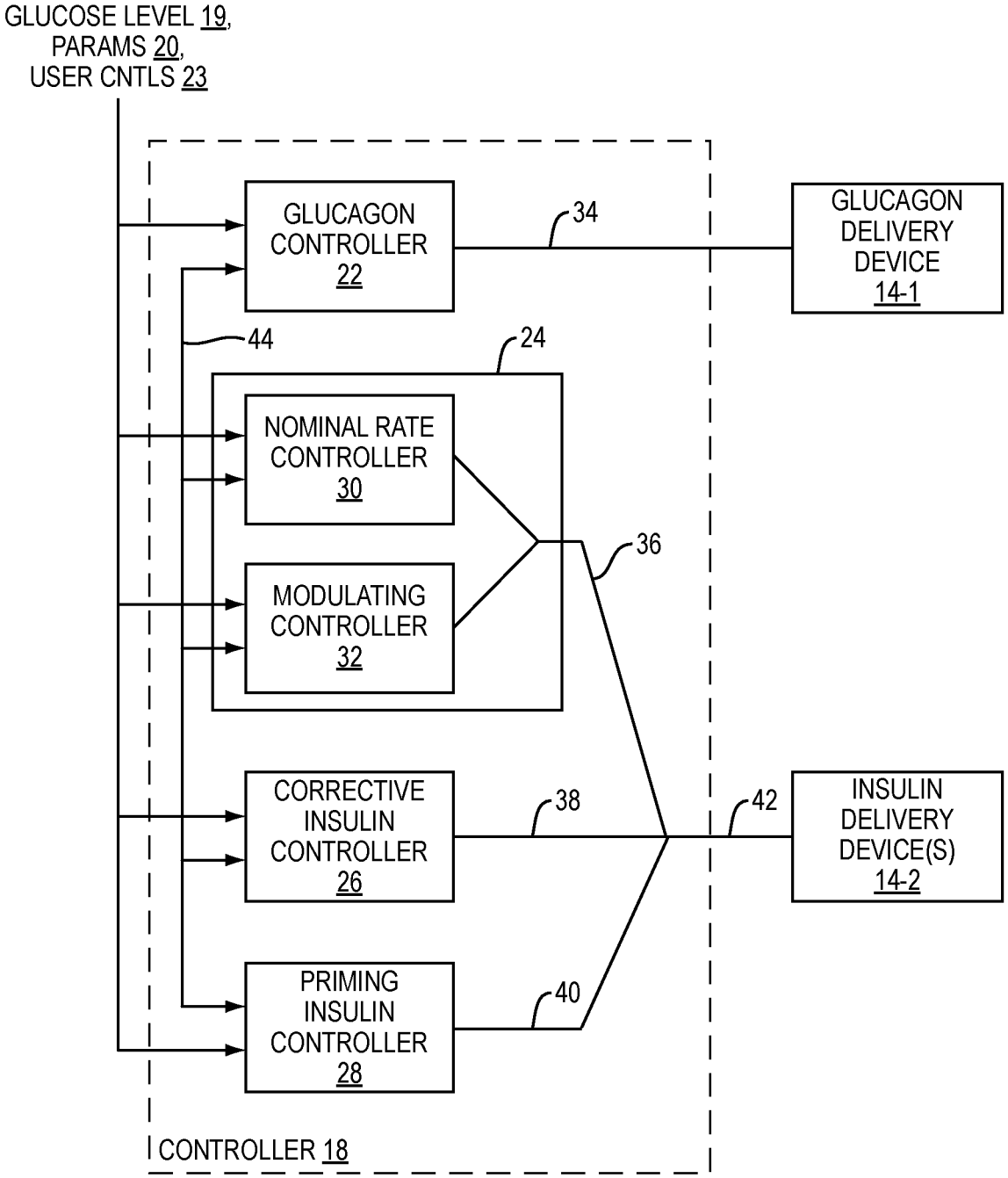
FIG. 2 is a block diagram of a controller.

FIG. 2 shows the structure of the controller 18. It includes four separate controllers, namely a glucagon controller 22, basal insulin controller 24, corrective insulin controller 26, and priming insulin controller 28. The basal insulin controller 24 includes a nominal rate controller 30 and a modulating controller 32. As shown, the glucagon controller 22 generates a glucagon dose control signal 34 provided to a glucagon delivery device 14-1. Respective outputs 36-40 from the controllers 24-28 are combined to form an overall insulin dose control signal 42 provided to insulin delivery device(s) 14-2. As shown, the output signal 36 from the basal insulin controller 24 is formed by a combination of respective outputs of the nominal rate controller 30 and modulating controller 32. The insulin delivery device(s) 14-2 may include devices tailored to deliver different types and/or quantities of insulin, with the exact configuration being known to and under the control of the controllers 24-28. For ease of description the collection of one or more insulin delivery devices 14-2 is referred below to in the singular as an insulin delivery device 14-2.

Also shown in FIG. 2 are input/output signals of the various controllers, including the glucose level signal 19, parameters 20 and user inputs 23 as well as a set of inter-controller signals 44. The inter-controller signals 44 enable communication of information from one controller, where the information is developed or generated, to another controller where the information is used for that controller's control function.

The controllers 22-28 may be operated in either the online/automatic mode or in the offline mode. In the automated mode, the corrective controller 26 regulates glucose level using a control scheme such as described in US patent publication 2008/0208113A1, the contents of which are incorporated by reference herein. The basal controller 24 and priming insulin controller 28 may perform adaptive automated control as described in international patent application publication WO 2012/058694 A2, the contents of which are incorporated by reference herein. The controllers 22-28 generally employ control methods or algorithms that include control parameters that are mathematically combined with reported glucose values to generate an output value that is converted (either directly or via additional conditioning) into the dose control signals 34, 42. For example, the control scheme described in US patent publication 2008/0208113A1 includes a generalized predictive control (GPC) method that incorporates a variety of control parameters. The control algorithms are generally adaptive, meaning that control parameters are dynamically adjusted during operation to reflect changing operating circumstances and a "learning" aspect—by monitoring its own operation, the algorithm adjusts its operation to be more specifically tailored to the individual user, enhancing the algorithm's effectiveness and reducing or avoiding a need for additional explicit input information about the user. It should be noted that the input parameters 20 form part of the control parameters used by the control algorithm; other control parameters are internal parameters according to the specifics of the algorithm, and selected ones of those internal control parameters are dynamically adjusted to realize the adaptation of the control algorithm.

One feature of operation is the ability of the controllers to learn from recent past periods of online operation and to use that learning during offline operation. Specifically, described below are two methods that are usable independently or together in offline operation. A first method automatically calculates the correct size of a correction bolus of insulin at a time of receiving an isolated glucose measurement, the correction bolus then being administered by the system in response to a user control input. A second method automatically calculates the correct size of a meal bolus of insulin and administers it in response to a user control input. Both methods utilize information obtained during past periods of online operation to automatically calculate correct values, freeing the user of a need to make the calculation or provide a correction factor.

I. Automatically Calculated Correction Bolus During Periods of Offline Operation The method for automatically calculating a correction bolus dose in real time during offline operation is achieved by invoking an online control algorithm individually on isolated glucose measurements as they are provided to the control system 10 during offline operation. These isolated glucose measurements may be blood glucose (BG) measurements from a glucose meter of any kind or glucose measurements obtained from another glucose monitor of any kind, provided to the control system 10 via the user controls 23. The automatic calculation of the correction bolus doses follows the same method described for continuous online control in the above-referenced US patent publication 2008/0208113A1, treating each isolated glucose measurement provided during offline operation as if it were a glucose value obtained from the glucose level signal 19. Effectively, each correction bolus operation is a brief resumption of online control. Time gaps in glucose data are taken into account by the online algorithm in its calculations of the effective rate of change of glucose as well as the overall outstanding insulin accumulation when the online algorithm is invoked in real time around the isolated glucose measurements. In particular, during offline operation the algorithm continues to mark the passage of time as a succession of sampling intervals in which it does not receive glucose sensor input and it does not generate regular correction doses of insulin. It continues to model the diminishing of on-board insulin level in the subject 12 over time, so that at any given time it has an accurate estimate of the future effect of previously administered insulin. When the controller 18 receives an isolated glucose measurement from the user along with an instruction to generate a correction dose, the algorithm performs an interpolation between the current glucose measurement and the most recent glucose sample value (from a preceding period of online control or isolated glucose measurement) to obtain estimated glucose values for recent sampling intervals as needed for the algorithm's computations.

In one embodiment the system may request user confirmation before delivering the automatically calculated correction bolus, while in other embodiments it may not request confirmation or there may be a configuration setting to control whether confirmation is requested. Similarly, the system may or may not disclose the dosing amount to the user, and/or may allow the user to modify the dosing amount (these behaviors also being configurable in one embodiment).

Figure 3:
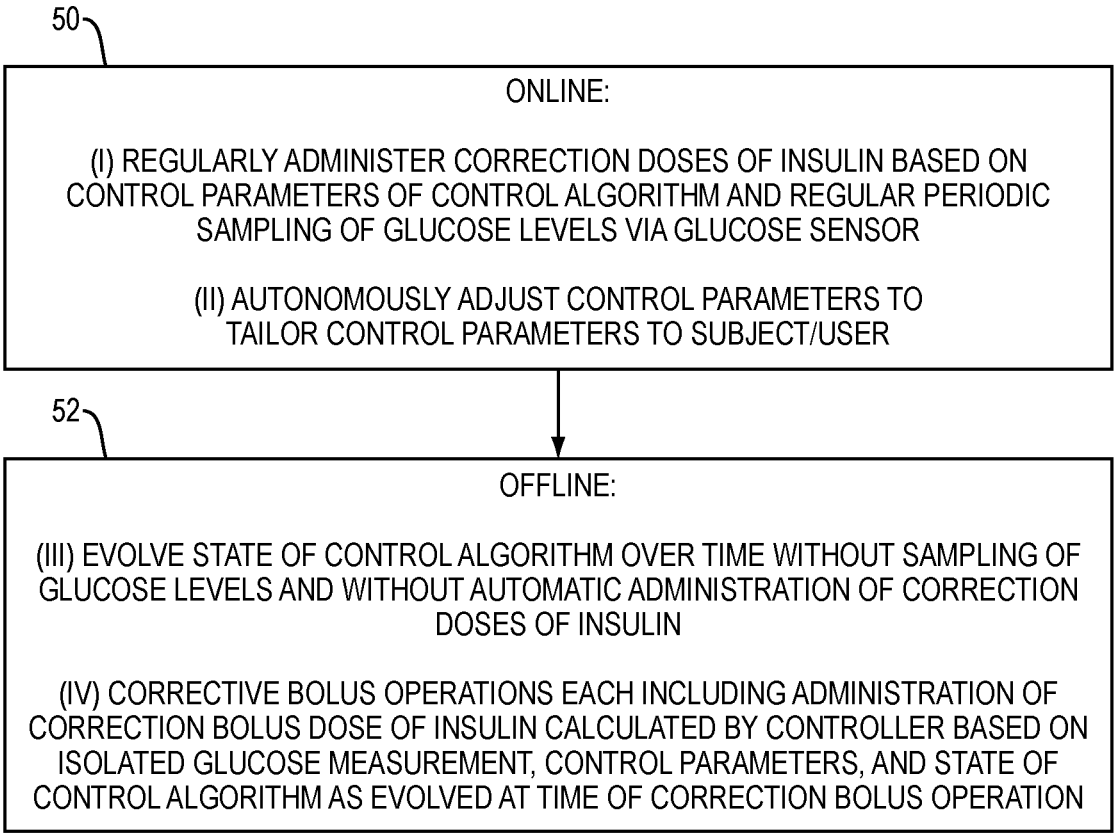
FIG. 3 is a flow diagram of a first method of operation of the system.

FIG. 3 illustrates high-level operation of the method for automatically calculating a correction bolus dose. At 50, during online operation the controller 18 employs a control algorithm that includes (i) regularly administering correction doses of insulin based on control parameters of the control algorithm and regular periodic sampling of glucose levels via the glucose sensor, and (ii) autonomously adjusting the control parameters to tailor the control parameters to the subject. As mentioned, this operation may be in accordance with the above-referenced US patent publication 2008/0208113A1.

At 52, the controller 18 engages in offline operation that includes (iii) evolving a state of the control algorithm over time without sampling of glucose levels and without automatic administration of the correction doses of insulin, and (iv) correction bolus operations each including administering a correction bolus of that is calculated by the controller based on the isolated glucose measurement, the control parameters, and a state of the control algorithm as evolved at the time of the correction bolus operation. In this description, the term "correction bolus operation" is used for convenience; this operation may alternatively be referred to using the more general term "correction dosing operation."

The correction bolus may be calculated by the controller 18 during offline operation assuming a first target glucose level or range higher than a second target glucose level or range assumed during online operation. Additionally, the correction dose of insulin may be calculated by the controller 18 during periods when the counter-regulatory delivery channel or device 14-1 is unavailable, and assuming a first target glucose level or range higher than a second target glucose level or range assumed when the counter-regulatory delivery channel or device is available.

Additional details of the method for automatically calculating a correction bolus dose during offline operation and its effects are now provided with reference to data generated by simulations of operation based on assumed characteristics of a subject or user.

FIGS. 4-7 show results of simulations illustrating the proposed automatic normalized correction bolus dose action when the controller 18 is offline, using arbitrary parameters in the control system 10. In addition to illustrating the proposed approach, these simulations also demonstrate the stability and added safety of this method, as it removes the vulnerability of the system that could arise from subjective dosing estimation by the user during isolated periods when the controller 18 is offline. As an enabling example, the simulations in these figures use controller, glucose data, and blood-glucose (BG) data that may resemble data from an experiment in a clinical study.

Figure 4:
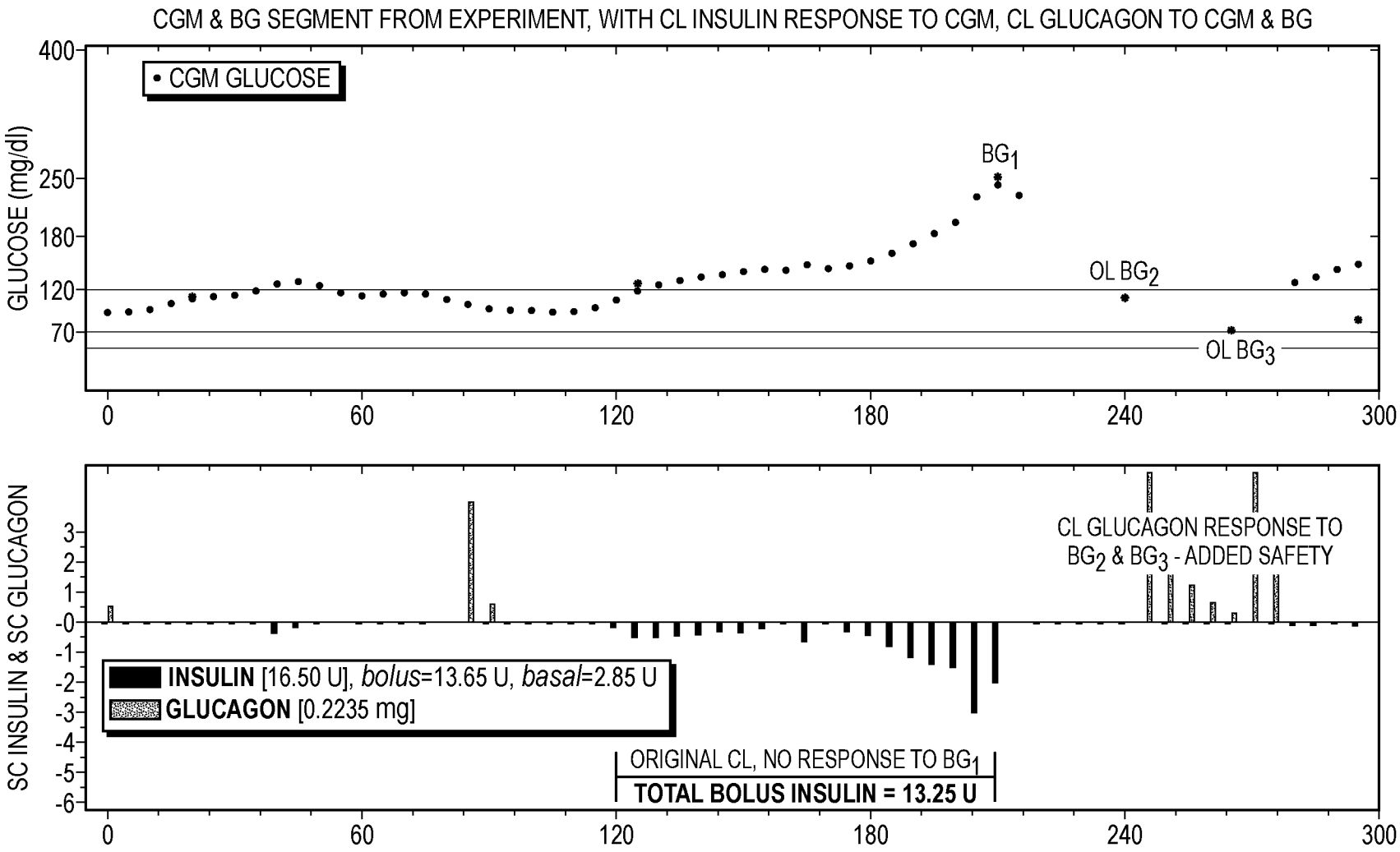
FIG. 4 is a graph depicting results of simulation of operation as a baseline for comparison with other simulations.

FIG. 4 shows a scenario in which regular online operation is occurring up to a time that a user provides a BG value BG1 as an input that is ignored by the control system 10, and then the control system 10 is taken offline. This simulation provides a reference online insulin response for comparison with responses when the control system 10 uses BG1 to automatically calculate a correction bolus of insulin. In this simulation, the control system 10 administers a total bolus insulin of 13.25 U to counter the hyperglycemic excursion that is occurring at the time of the BG1. In these figures the euglycemic band between 70 and 120 is indicated by shading.

Figure 5:
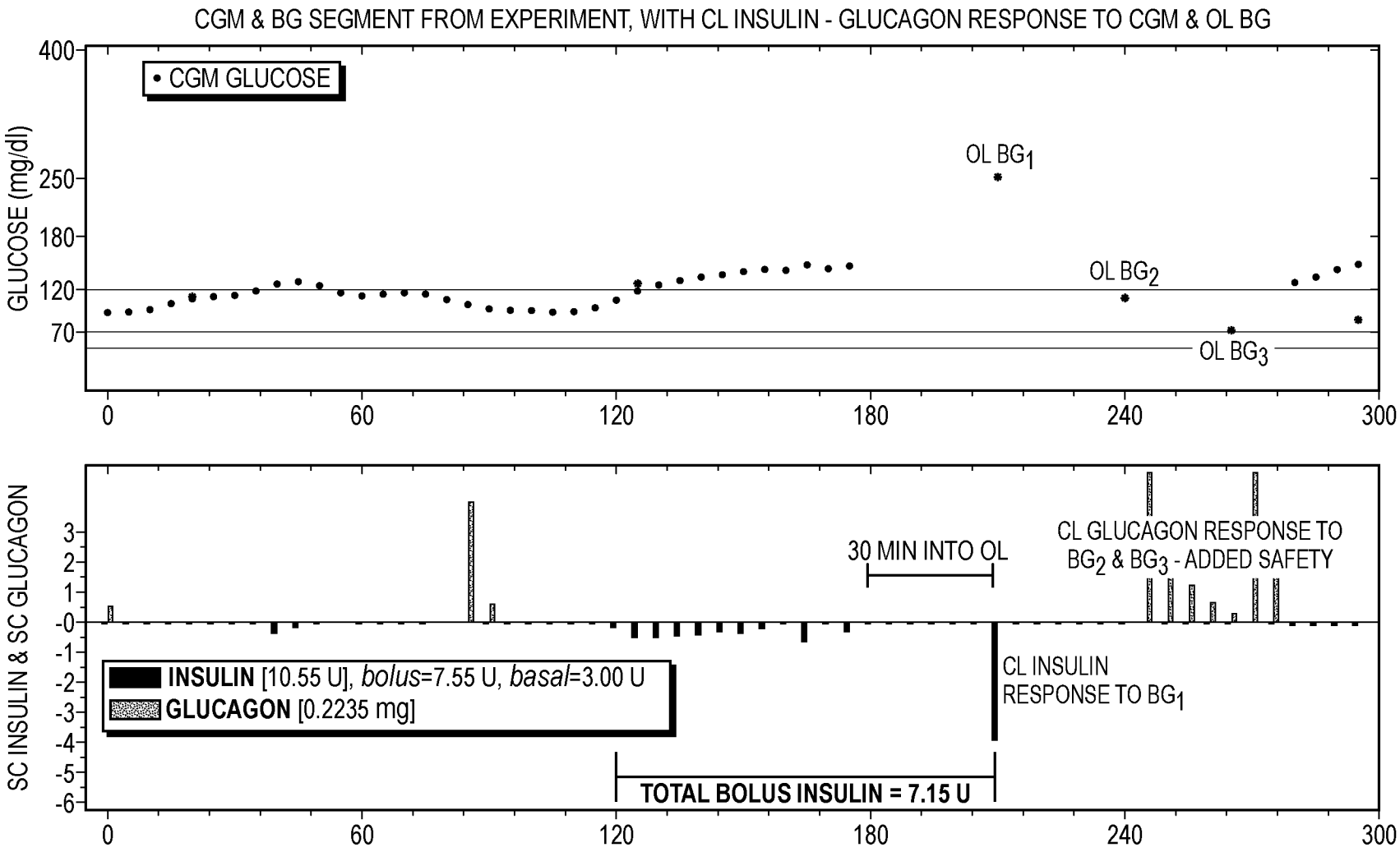
FIGS. 5-8 are graphs depicting results of simulations of operation according to the method of FIG. 3.
Figure 6:
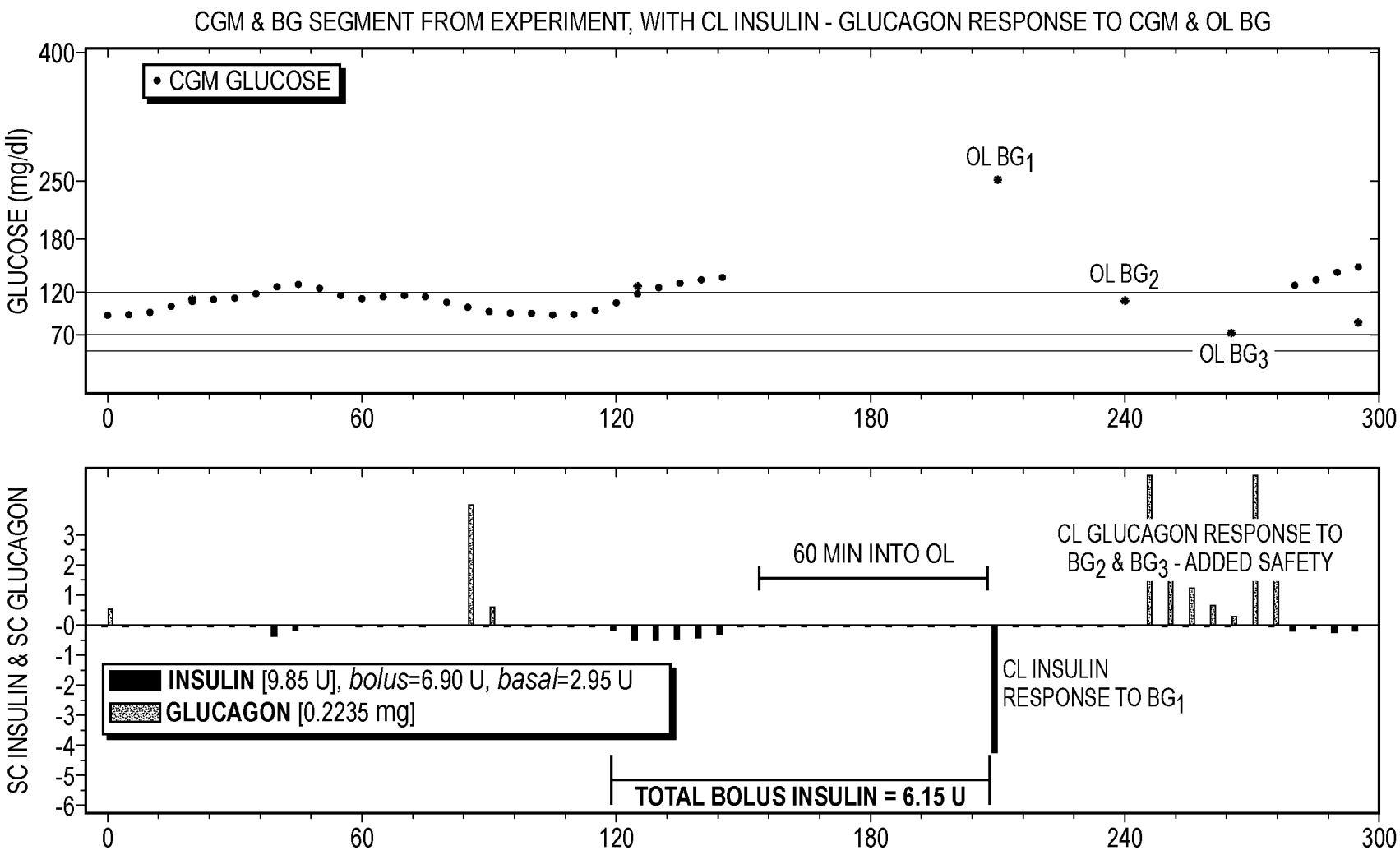
Figure 7:
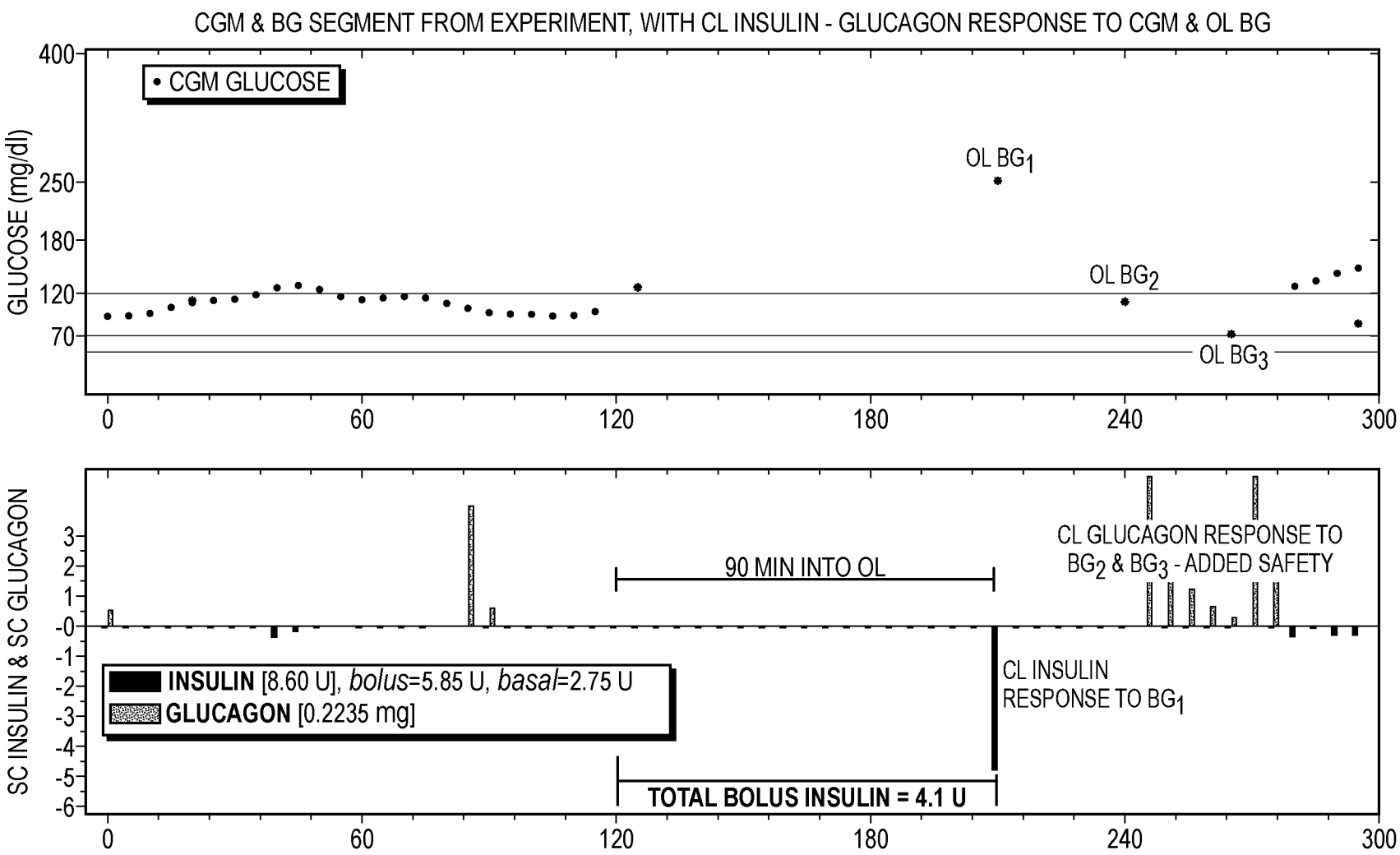

FIGS. 5-7 show insulin responses when the method of FIG. 3 is used, specifically in these cases to respond to the user-entered BG1 value. Such an automated BG-based correction bolus response replaces the conventional practice in which the user calculates insulin correction bolus doses during isolated offline periods based on what the user estimates to be their "correction factor". However, such a correction factor can be subjectively selected, and in not even be known to a newly diagnosed user. Moreover, its use may put the control system 10 in jeopardy or in a vulnerable state if inappropriately estimated by the user, particularly if the value is excessive. Note that user action is only required to obtain and enter BG values, an activity that is always necessary to determine correction doses if there is no automated sensing of glucose levels (e.g., during offline operation).

FIG. 5 shows one simulation in which a correction bolus of insulin is automatically calculated by the control system 10 in response to user-entered BG1 after an offline period of 30 minutes. The total correction insulin over the hyperglycemic excursion leading to BG1 is 7.15 U, which is more conservative than the pure online response of FIG. 4. A more realistic simulation might account for the period of offline operation prior to BG1 by having the BG level drift higher. However, it is estimated that even if BG1 were greater than 400, total correction insulin that would be delivered is only 12.65 U, which is still more conservative than the pure online response in FIG. 4 and therefore safer, particularly because it inevitably comes later with BG already in severe hyperglycemia. It should be noted that the control system 10 may enforce an upper limit on the value of a BG measurement it will use, such as 400. The user interface might enforce this limit.

FIGS. 4 and 5 also show automatic glucagon correction doses in response to BG2 and BG3. This provides added safety by the system and is a response that is not available in usual care. Note how the control system 10 responds with glucagon correction doses to BG2, even though it is near the high end of normal range—this is because BG2 indicates a downward trend in glucose from BG1. This trend is verified by BG3 being near the low end of normal range, which triggers further glucagon correction doses.

FIGS. 6 and 7 show the correction bolus of insulin automatically calculated by the control system 10 in response to user-entered BG1 after offline periods of 60 and 90 minutes, respectively. The latter case in essence shows the response when the hyperglycemic excursion occurs entirely while the control system 10 is offline. The total bolus insulin over the hyperglycemic excursion leading to BG1 is 6.15 U and 4.1 U respectively, which in both cases is more conservative than the purely controller-based insulin response in FIG. 4. As above, a more realistic simulation would show a higher BG value at the time of the BG1 sample. However, it is estimated that even if BG1 were greater than 400, total correction insulin would be only 11.15 U and 10.05 U, respectively, which in both cases is more conservative than the pure online response. These figures also show automatic glucagon correction doses in response to BG2 and BG3, similar to the responses in FIGS. 4 and 5.

Figure 8:
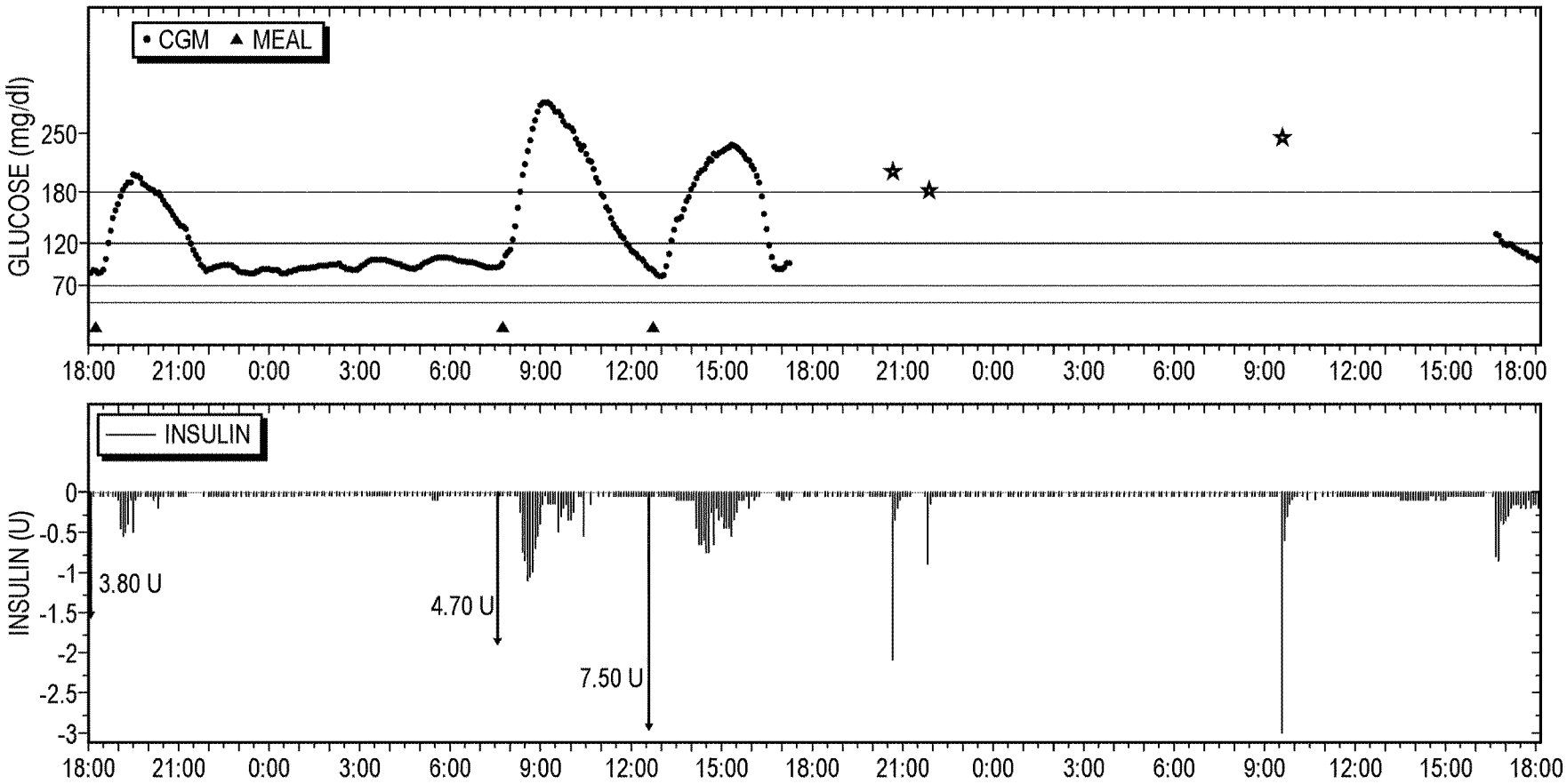

FIG. 8 provides data from a simulation using different controller and BG data, which is also used for illustration of the meal bolus method in the next section below, as well as for the superposition of the two methods also described below. Also, a longer overall period is shown. Specifically, FIG. 8 shows a sample simulation illustrating the method of automatically calculating correction bolus doses in real time during offline operation (in this example, from 17:30 to 16:30 across two consecutive days) individually based on isolated glucose measurements that are provided to the control system 10 during online operation (e.g. blood glucose measurements from a glucose meter or glucose measurements obtained from another glucose monitor). The top panel shows the glucose trace (as black circles) during online operation and times of meals (indicated by black triangles), with additional glucose measurements (indicated by gray stars) that were provided by the user to the control system 10 during offline operation. The bottom panel shows automatically generated correction insulin doses as slender gray bars. Also shown are meal bolus doses indicated by isolated gray strikes with arrowheads—these are described in a separate section below.

During online periods in the simulation of FIG. 8, insulin doses include bolus and basal doses generated by the online algorithm as well as (potential) meal bolus doses, whereas during offline operation, insulin doses include algorithm-generated basal doses as well as automatically calculated correction bolus doses. Each correction bolus dose during offline operation is automatically calculated by invoking the online control algorithm individually on the isolated glucose measurements in real time as they are provided to the control system 10, as described above. In real operation, both online and offline periods are generally different from the arbitrarily chosen spans in this example, and each can contain intermittent segments of the other within its span.

II. Automatically Calculated Meal Bolus Dose During Periods of Offline Control

A method is also described for automatically calculating a meal bolus dose in real time during offline operation by an online control algorithm based on the prandial and post-prandial response(s) during preceding period(s) of online operation when a meal bolus was administered for a meal or snack of the corresponding kind and/or time interval of day (breakfast, lunch, or dinner). The automatic calculation from preceding period(s) of online operation could include multiple incidents of each kind of meal bolus dose (e.g. multiple days having occasions of breakfast, lunch, or dinner). The automatic calculation of the meal bolus doses during offline operation may follow the same method described in the above-referenced international patent application publication WO 2012/058694 A2 for its implementation during online operation, i.e. meal bolus doses are adapted based on online operation and in this case are issued in the same way during offline operation as they are during continual online operation.

Figure 9:
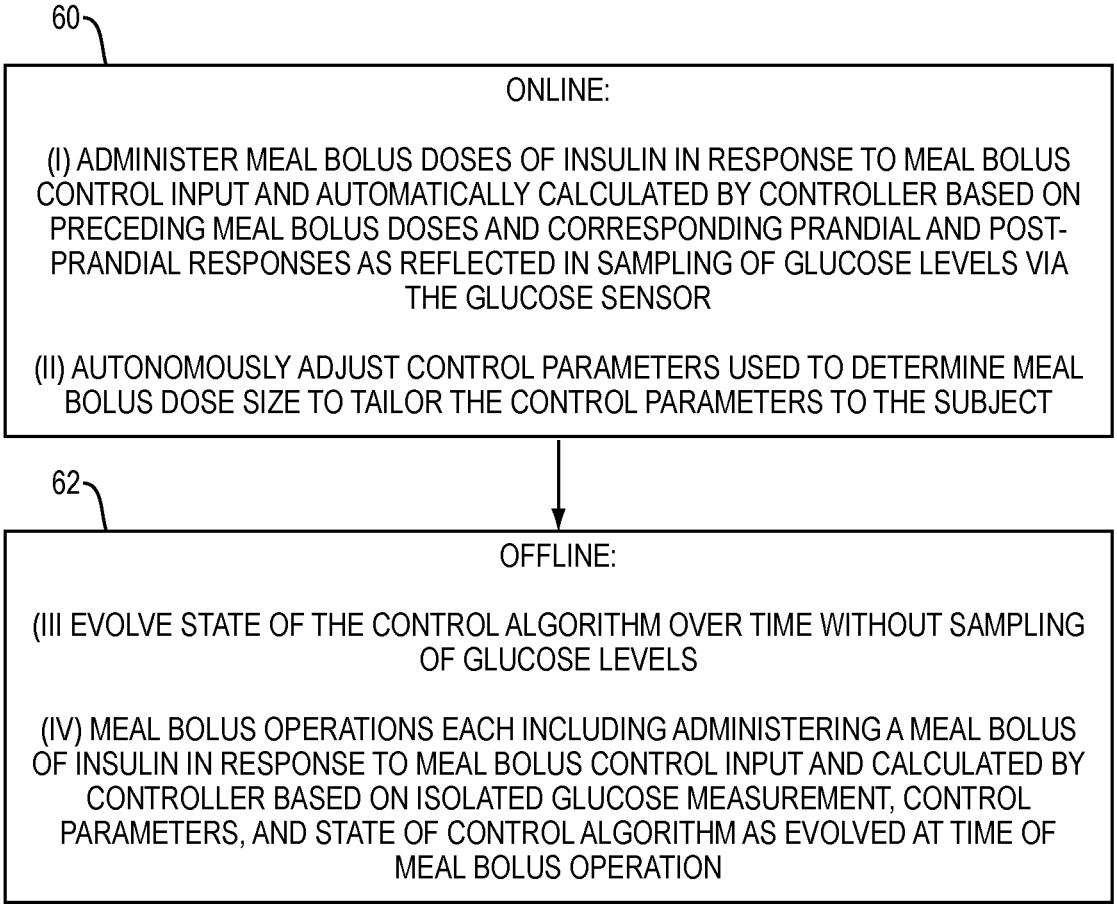
FIG. 9 is a flow diagram of a second method of operation of the system.

FIG. 9 illustrates high-level operation of the method for automatically calculating a meal bolus dose during offline operation. At 60, during online operation the controller 18 employs a control algorithm that (i) administers meal bolus doses of insulin in response to a meal bolus control input and automatically calculated by the controller 18 based on preceding meal bolus doses and corresponding prandial and post-prandial responses of the subject 12 as reflected in sampling of glucose levels via the glucose sensor and (ii) autonomously adjusts control parameters used to determine meal bolus dose size to tailor the control parameters to the subject.

At 62, offline operation includes (iii) evolving a state of the control algorithm over time without sampling of glucose levels, and (iv) meal bolus operations each including administration of a meal bolus of insulin in response to the meal bolus control input and calculated by the controller based on the isolated glucose measurement, the control parameters, and a state of the control algorithm as evolved at the time of the meal bolus operation. The meal bolus may be administered in one continuous ejection or discharge from the insulin pump, or it may be administered as multiple ejections over a short period (e.g., split over consecutive sampling intervals). Some pumps enforce a limit for a single ejection, so if the bolus to be delivered exceeds that limit then it may be delivered using multiple ejections over a short period (e.g., split over consecutive sampling intervals). In this description, the term "meal bolus operation" is used for convenience; this operation may alternatively be referred to using the more general term "meal dosing operation."

Figure 10:
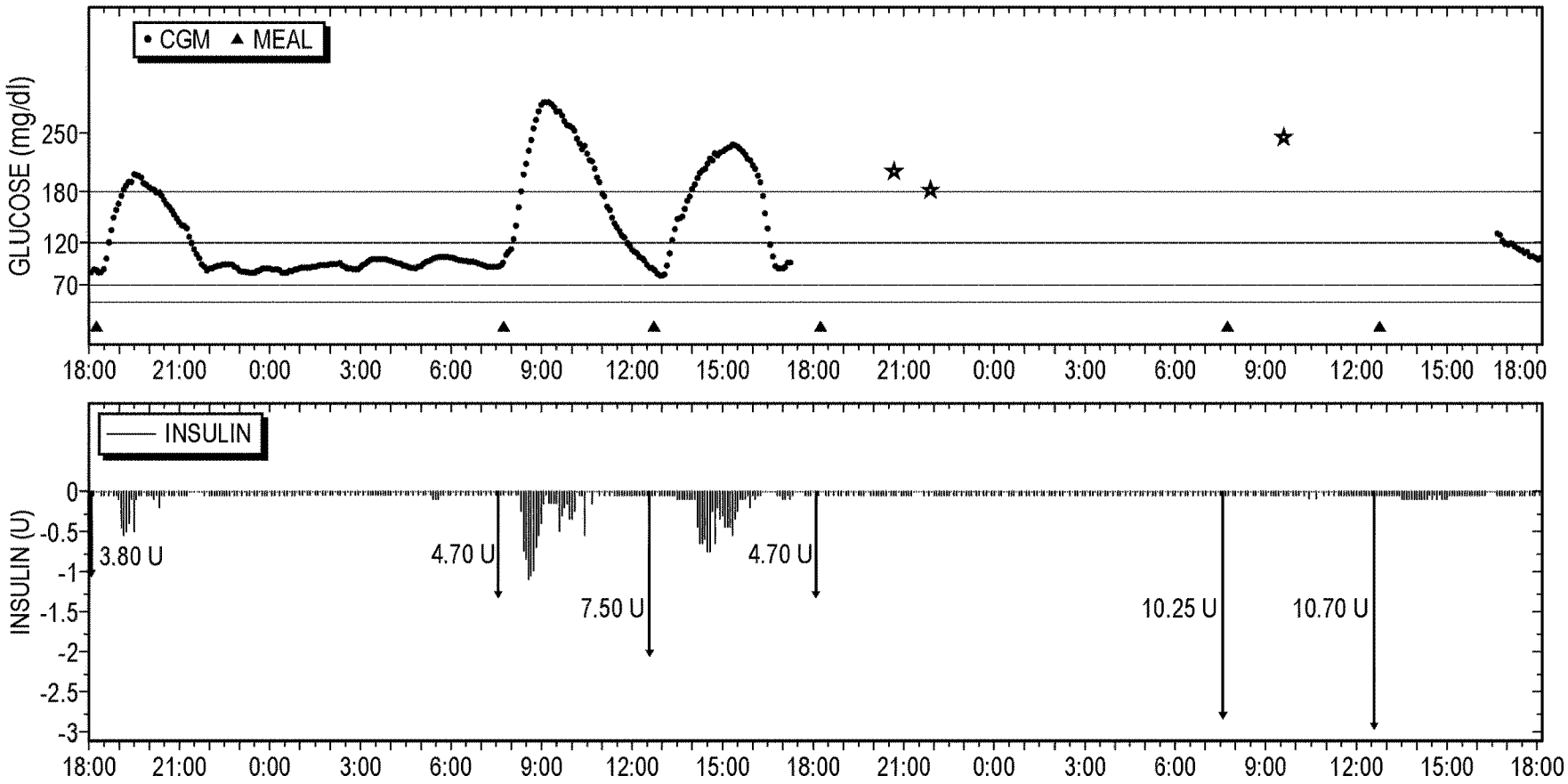
FIG. 10 is a graph depicting results of a simulation of operation according to the method of FIG. 9.

FIG. 10 provides a sample illustration of the described method. This uses the controller and BG data that was also used for illustration of the correction bolus method in FIG. 8. Note that the inherent learning and adjusting of meal bolus doses in this method can continually undergo online adjustments with more periods of online control. The system may or may not request user confirmation before delivering the automatically calculated meal bolus, may or may not disclose the dosing amount to the user, and may or may not allow the user to modify the dosing amount.

More specifically, FIG. 10 shows a sample simulation illustrating the method of automatically calculating meal bolus doses in real time during offline operation (in this example, from 17:30 to 16:30 across two consecutive days) based on meal bolus doses and their corresponding prandial and post-prandial responses during preceding online operation (in this example, from a preceding period of 18:00 to 17:30 across two consecutive days). The top panel shows the glucose trace (as black circles) during online operation and times of meals (indicated by black triangles). The bottom panel shows automatically generated insulin doses as slender gray bars, with meal bolus doses (as they are triggered or announced by the user) indicated by isolated gray strikes with arrowheads. During online operation, insulin doses include correction boluses and basal doses generated by the online algorithm as well as meal bolus doses, whereas during offline operation, insulin doses include algorithm-generated basal doses and automatically calculated meal bolus doses. Each meal bolus dose during offline operation was automatically calculated by the online algorithm based on the prandial and post-prandial response(s) during preceding period(s) of online operation when a meal bolus was administered for a meal or snack of the corresponding kind and/or time interval of day (breakfast, lunch, or dinner). The automatic calculation from preceding period(s) of online operation could include multiple incidents of each kind of meal bolus dose (e.g. multiple days having multiple occasions of breakfast, lunch, or dinner). The inherent learning and adjusting of meal bolus doses in this method can continually undergo offline adjustments with more periods of online control. Also, both online and offline periods can vary in span from their arbitrarily chosen spans in this example, and each can contain intermittent segments of the other within its span.

Note that the user may choose not to utilize the meal bolus dose option when in online operation, as the control algorithm is able to automatically respond to prandial or post-prandial glucose excursions when in online operation. However, such an automatic online response will be absent or ineffective if the prandial or post-prandial period occurs when in offline operation. Therefore, good glycemic control generally requires using the meal bolus dose option around the times of food consumption during offline operation. Since the meal bolus dose is effectively adapted during online operation, it follows that in order to get optimal control when using it during offline operation, the user should occasionally, if not regularly, use the meal bolus dose option in online operation. Occasional utilization could be on the order of once per week for a couple of weeks for each kind and/or time interval of day (breakfast, lunch, or dinner), but could also be more or less frequent than that, and/or altogether on an irregular time basis. Such occasional online usage over time allows for repeated adaptations of the meal bolus dose, which essentially updates the meal bolus dose magnitude(s) to better suit the user's needs based on their own determinations of the relative size of meals. In summary, while the meal bolus dose option may or may not be necessary for effective control under online operation, using it (at least occasionally) during online operation allows adapting the meal bolus dose magnitude(s) so as to be more effective when used in offline operation.

Superposition of the Two Methods

Figure 11:
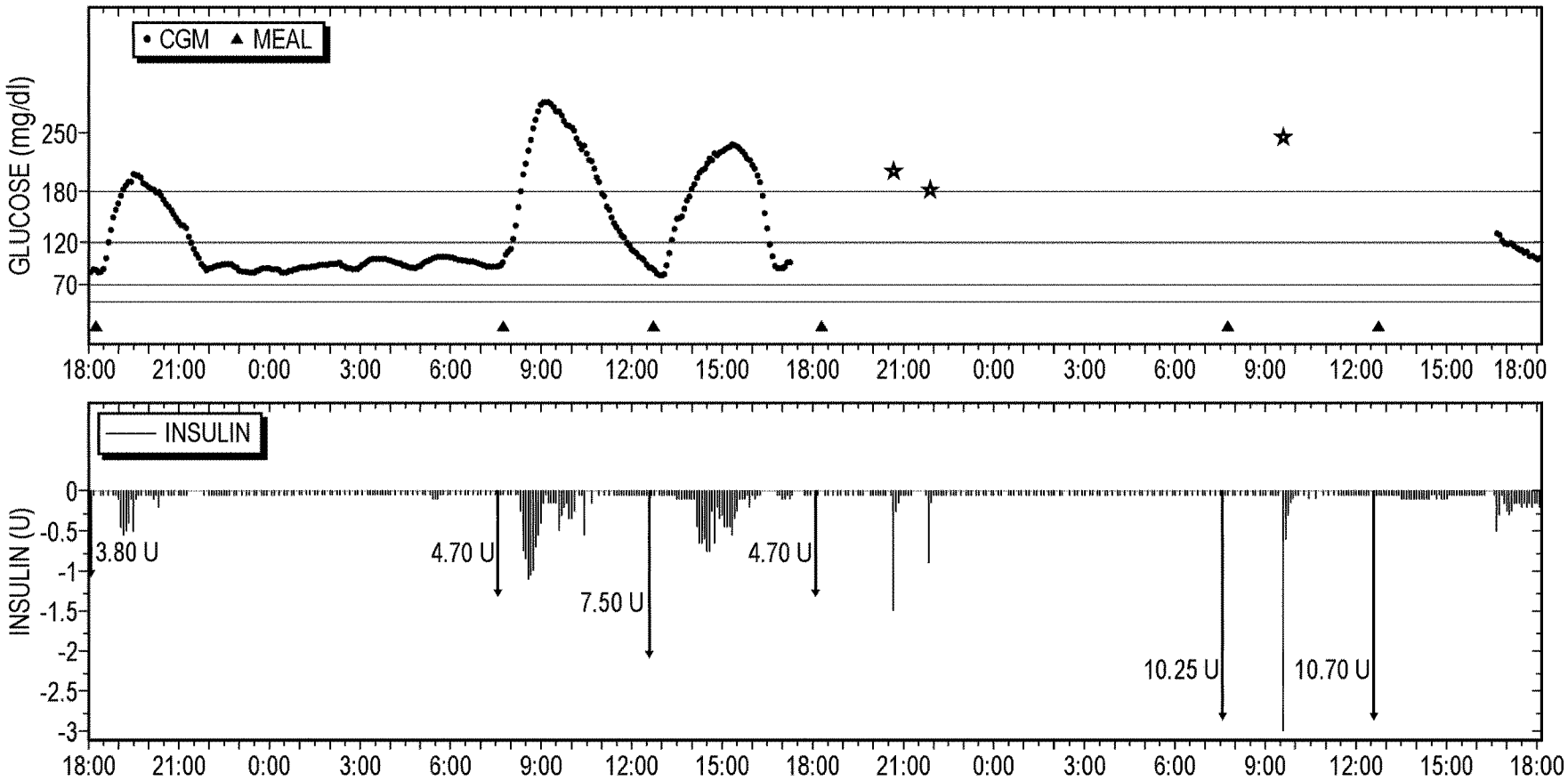
FIG. 11 is a graph depicting results of simulation of operation according to both the methods of FIG. 3 and FIG. 9.

FIG. 11 shows an example in which both the methods of (1) automatically calculating correction bolus doses of insulin and (2) automatically calculating meal bolus of insulin in real time during online operation are used together. This simulation uses the controller and BG data that was also used for illustrations of the correction bolus and meal bolus methods described above.

Other Control Aspects

Independently, the control system 10 can, in a similar manner, automatically calculate in real time a correction bolus dose of a counter-regulatory agent (such as glucagon) during online operation. With a counter-regulatory agent being available for use by the control system 10, offline operation action around an isolated glucose measurement could include real-time doses of the counter-regulatory agent. The system can still issue a correction bolus of insulin in an independent manner, so that it can exercise both correction bolus kinds (insulin and glucagon) or one kind without the other.

Figure 12:
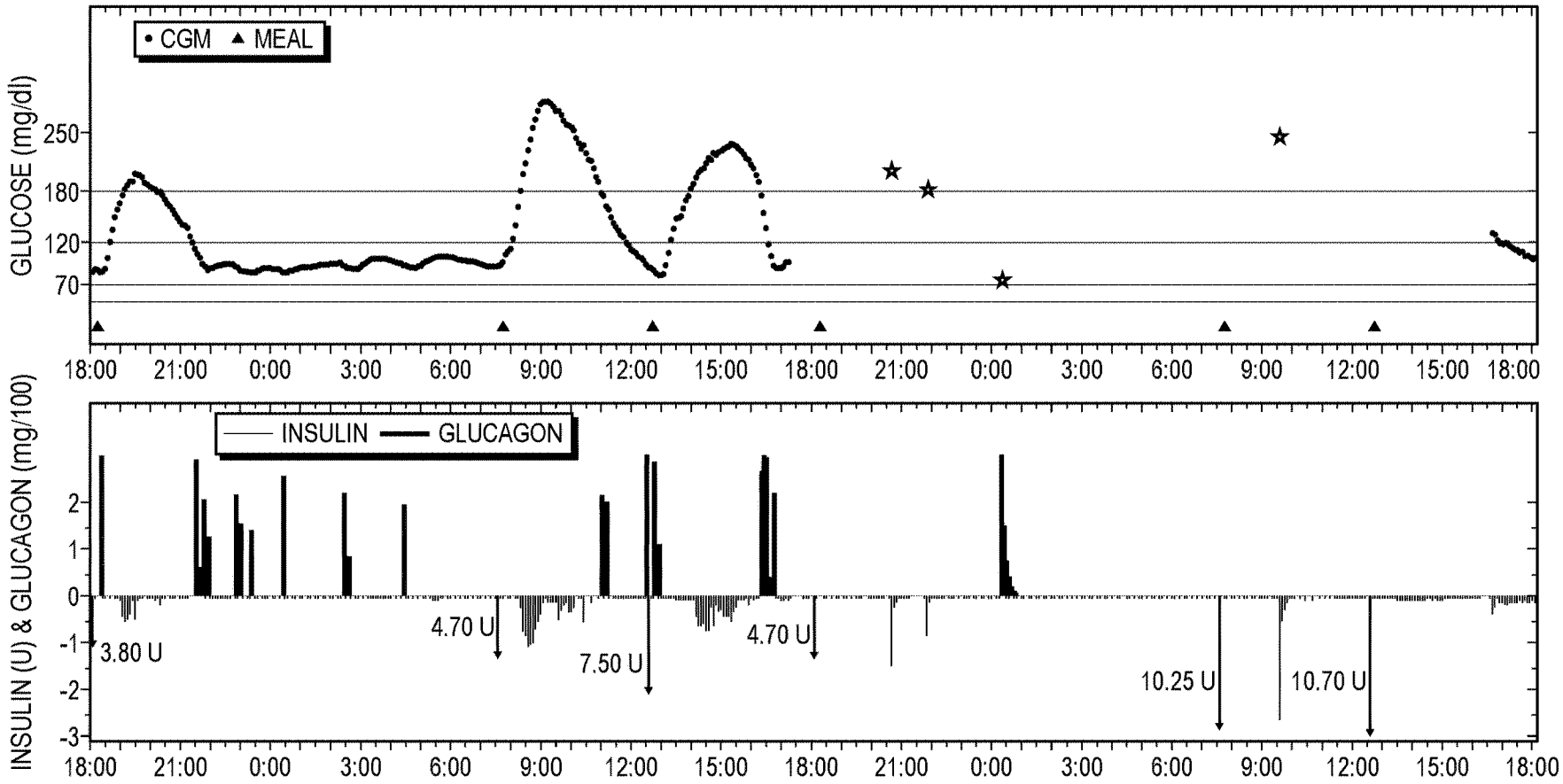
FIG. 12 is a graph depicting results of simulation of operation incorporating use of a counter-regulatory agent.

FIG. 12 shows an example, using glucagon as the counter-regulatory agent, in which the system automatically calculates both kinds of correction bolus doses (insulin and glucagon). The correction bolus doses of insulin are arbitrarily chosen to be at the same times as those in FIG. 8, and correction bolus action of glucagon is illustrated in the simulation at around 00:30 on the second day, where a glucose measurement that is near the low end of normal range was provided to the control system 10. The system could also respond with counter-regulatory correction bolus action for higher or lower glucose measurement, depending on each individual situation and the control algorithm used. The automatic calculation of the counter-regulatory correction bolus doses may follow the same method described for continuous online control in the above-referenced US patent publication 2008/0208113A1, treating the correction and meal bolus operations as brief resumption of online control as described above. Additionally, the system may include an ability to readily deliver a (default) preset counter-regulatory correction bolus (e.g. in cases of emergency). With these methods all superimposed as they are in FIG. 12 (along with invoking automated basal insulin infusion during online operation, as per the disclosure in US patent application publication 20130245547A1), periods of online operation include algorithm-generated correction bolus doses of insulin and glucagon, meal bolus doses of insulin, and basal doses of insulin, all automatically calculated by the controller 18.

In both the online and offline operations, the control algorithm may allow the subject to issue a microburst or rescue dose of counter-regulatory agent, with a value of the microburst or rescue dose being calculated by the controller 18.

All of the methods described above could be used in the in-patient (e.g. critical care units or general wards, where the route of drug administration could vary and where dextrose is an example of a counter-regulatory agent) or out-patient settings and could be used in the context of an autonomous or semi-autonomous online glucose control system 10 (e.g. sensor-augmented infusion system). The methods could also be applied in online operation separately or in conjunction in various combinations. When employed in online operation, these methods could ultimately render obsolete notions of requiring the user (or care provider) to know and set control parameters such as insulin-to-carbohydrate ratios, correction factors (for both insulin or insulin-like agent and a counter-regulatory agent), as well as basal rates of insulin infusion.

While various embodiments of the invention have been particularly shown and described, it will be understood by those skilled in the art that various changes in form and details may be made therein without departing from the spirit and scope of the invention as defined by the appended claims.

What is claimed is:

1. A glucose level control system, comprising:

a glucose sensor operative to continually measure a glucose level of a subject and generate a corresponding glucose level signal;

an insulin delivery device operative in response to an insulin dose control signal to infuse insulin into the subject; and a controller having online operation and offline operation to generate the insulin dose control signal to achieve and maintain euglycemia in the subject, online operation employing a control algorithm including (i) regular administration of correction doses of insulin based on control parameters of the control algorithm and regular periodic sampling of glucose levels via the glucose sensor, and (ii) autonomously adjusting the control parameters to tailor the control parameters to the subject, offline operation including (iii) evolving a state of the control algorithm over time without sampling of glucose levels and without automatic administration of the correction doses of insulin, and (iv) correction dosing operations each including administration of a correction dose of insulin in response to an isolated glucose measurement provided to the controller, the correction dose being calculated by the controller based on the isolated glucose measurement, the control parameters, and a state of the control algorithm as evolved at the time of the correction dosing operation.

2. A glucose level control system according to claim 1, wherein the control algorithm employs regular periodic sampling intervals, and wherein evolving the control algorithm during the offline operation includes updating time effects of insulin previously administered to the subject.

3. A glucose level control system according to claim 2, wherein each correction dose during the offline operation includes calculating estimated glucose levels for immediately preceding offline sampling intervals using interpolation between a current isolated glucose measurement and a sample of glucose level from a most recent period of online operation.

4. A glucose level control system according to claim 1, wherein the correction dose is calculated by the controller during the offline operation assuming a first target glucose level or range higher than a second target glucose level or range assumed during online operation.

5. A glucose level control system according to claim 1, wherein the isolated glucose measurement is provided to the controller via a user interface used by the subject, and wherein each correction dosing operation includes use of one or more user interface functions selected from (i) the subject confirming that the correction dose is to be delivered, (ii) displaying the value of the correction dose to the subject, and (iii) accepting a modified value from the subject for use as the correction dose instead of the correction dose calculated by the controller.

6. A glucose level control system according to claim 1, wherein online operation of the control algorithm further includes regular administration of correction doses of a counter-regulatory agent based on the control parameters of the control algorithm and the regular periodic sampling of glucose levels, and wherein the offline operation further includes counter-regulatory agent dosing operations each including administration of a dose of a counter-regulatory agent in response to a second isolated glucose measurement provided to the controller and calculated by the controller based on the second isolated glucose measurement, the control parameters, and the state of the control algorithm as evolved at the time of the counter-regulatory agent dosing operation.

7. A glucose level control system according to claim 6, wherein the correction dose of insulin is calculated by the controller during periods when a counter-regulatory delivery channel or device is unavailable and assuming a first target glucose level or range higher than a second target glucose level or range assumed when the counter-regulatory delivery channel or device is available.

8. A glucose level control system according to claim 1, wherein in both the online and offline operations, the control algorithm allows the subject to issue a microburst or rescue dose of counter-regulatory agent, a value of the microburst or rescue dose being calculated by the controller.

9. A glucose level control system according to claim 1, wherein online operation of the control algorithm includes (v) administration of meal doses of insulin in response to a meal dose control input and automatically calculated by the controller based on preceding meal doses and corresponding prandial and post-prandial responses of the subject as reflected in the sampling of glucose levels via the glucose sensor and (vi) autonomously adjusting control parameters used to determine meal dose size to tailor the control parameters to the subject, and wherein offline operation including meal dosing operations each including administration of a meal dose of insulin in response to the meal dose control input and calculated by the controller based on a second isolated glucose measurement, the control parameters, and the state of the control algorithm as evolved at the time of the meal dosing operation.

10. A method of operating a controller for a glucose level control system having a glucose sensor and an insulin delivery device, the glucose sensor being operative to continually measure a glucose level of a subject and generate a corresponding glucose level signal, the insulin delivery device being operative in response to an insulin dose control signal to infuse insulin into the subject, comprising:

performing online operation employing a control algorithm including (i) regular administration of correction doses of insulin based on control parameters of the control algorithm and regular periodic sampling of glucose levels via the glucose sensor, and (ii) autonomously adjusting the control parameters to tailor the control parameters to the subject; and performing offline operation including (iii) evolving a state of the control algorithm over time without sampling of glucose levels and without automatic administration of the correction doses of insulin, and (iv) correction dosing operations each including administration of a correction dose of insulin in response to an isolated glucose measurement provided to the controller, the correction dose being calculated by the controller based on the isolated glucose measurement, the control parameters, and the state of the control algorithm as evolved at the time of the correction dosing operation.

11. A method according to claim 10, wherein the control algorithm employs regular periodic sampling intervals, and wherein evolving the control algorithm during the offline operation includes updating time effects of insulin previously administered to the subject.

12. A method according to claim 11, wherein each correction dose during the offline operation includes calculating estimated glucose levels for immediately preceding offline sampling intervals using interpolation between a current isolated glucose measurement and a sample of glucose level from a most recent period of online operation.

13. A method according to claim 10, wherein the correction dose is calculated by the controller during the offline operation assuming a first target glucose level or range higher than a second target glucose level or range assumed during online operation.

14. A method according to claim 10, wherein the isolated glucose measurement is provided to the controller via a user interface used by the subject, and wherein each correction dosing operation includes use of one or more user interface functions selected from (i) the subject confirming that the correction dose is to be delivered, (ii) displaying a value of the correction dose to the subject, and (iii) accepting a modified value from the subject for use as the correction dose instead of the correction dose calculated by the controller.

15. A method according to claim 10, wherein online operation of the control algorithm further includes regular administration of correction doses of a counter-regulatory agent based on the control parameters of the control algorithm and the regular periodic sampling of glucose levels, and wherein the offline operation further includes counter-regulatory agent dosing operations each including administration of a correction dose of a counter-regulatory agent in response to a second isolated glucose measurement provided to the controller and calculated by the controller based on the second isolated glucose measurement, the control parameters, and the state of the control algorithm as evolved at the time of the counter-regulatory agent dosing operation.

16. A method according to claim 15, wherein the correction dose of insulin is calculated by the controller during periods when a counter-regulatory delivery channel or device is unavailable and assuming a first target glucose level or range higher than a second target glucose level or range assumed when the counter-regulatory delivery channel or device is available.

17. A method according to claim 10, wherein in both the online and offline operations, the control algorithm allows the subject to issue a microburst or rescue dose of counter-regulatory agent, a value of the microburst or rescue dose being calculated by the controller.

18. A method according to claim 10, wherein online operation of the control algorithm includes (v) administration of meal doses of insulin in response to a meal dose control input and automatically calculated by the controller based on preceding meal doses and corresponding prandial and post-prandial responses of the subject as reflected in the sampling of glucose levels via the glucose sensor and (vi) autonomously adjusting control parameters used to determine meal dose size to tailor the control parameters to the subject, and wherein offline operation including meal dosing operations each including administration of a meal dose of insulin in response to the meal dose control input and calculated by the controller based on a second isolated glucose measurement, the control parameters, and a state of the control algorithm as evolved at the time of the meal dosing operation.

19. A glucose level control system, comprising:

a glucose sensor operative to continually measure glucose level of a subject and generate a corresponding glucose level signal;

an insulin delivery device operative in response to an insulin dose control signal to infuse insulin into the subject; and a controller having online operation and offline operation to generate the insulin dose control signal to achieve and maintain euglycemia in the subject, online operation employing a control algorithm including (i) administration of meal doses of insulin in response to a meal dose control input and automatically calculated by the controller based on preceding meal doses and corresponding prandial and post-prandial responses of the subject as reflected in sampling of glucose levels via the glucose sensor and (ii) autonomously adjusting control parameters used to determine meal dose size to tailor the control parameters to the subject, offline operation including (iii) evolving a state of the control algorithm over time without sampling of glucose levels, and (iv) meal dosing operations each including administration of a meal dose of insulin in response to the meal dose control input and calculated by the controller based on an isolated glucose measurement, the control parameters, and a state of the control algorithm as evolved at the time of the meal dosing operation.

20. A glucose level control system according to claim 19, wherein online operation of the control algorithm further includes (i) regular administration of correction doses of insulin based on control parameters of the control algorithm and regular periodic sampling of glucose levels via the glucose sensor, and (ii) autonomously adjusting the control parameters to tailor the control parameters to the subject, and wherein the offline operation further includes (iii) evolving the state of the control algorithm over time without sampling of glucose levels and without automatic administration of the correction doses of insulin, and (iv) correction dosing operations each including administration of a correction dose of insulin in response to a second isolated glucose measurement provided to the controller, the correction dose being calculated by the controller based on the second isolated glucose measurement, the control parameters, and the state of the control algorithm as evolved at the time of the correction dosing operation.

*21. A controller for use in a glucose level control system having an insulin delivery device and a glucose sensor, the controller comprising:*

*processing circuitry including one or more processors;*

*memory; and*

*input/output circuitry,*

*the input/output circuitry providing respective interfaces to the insulin delivery device and the glucose sensor (1) to convey an insulin dose control signal to the insulin delivery device for controlling infusion of insulin into a subject, and (2) to receive a glucose level signal from the glucose sensor indicating a glucose level of the subject,*

*the memory storing computer program instructions executed by the processors to provide online operation and offline operation of the glucose level control system to generate the insulin dose control signal to achieve and maintain euglycemia in the subject, the online operation employing a control algorithm including (i) regular administration of correction doses of insulin based on control parameters of the control algorithm and regular periodic sampling of glucose levels via the glucose sensor, and (ii) autonomously adjusting the control parameters to tailor the control parameters to the subject, offline operation including (iii) evolving a state of the control algorithm over time without sampling of glucose levels and without automatic administration of the correction doses of insulin, and (iv) correction dosing operations each including administration of a correction dose of insulin in response to an isolated glucose measurement provided to the controller, the correction dose being calculated by the controller based on (i) the isolated glucose measurement, (ii) the control parameters, and (iii) the state of the control algorithm as evolved at the time of the correction dosing operation.*

*22. The controller of claim 21, wherein the control algorithm employs regular periodic sampling intervals, and wherein evolving the control algorithm during the offline operation includes updating time effects of insulin previously administered to the subject.*

*23. The controller of claim 22, wherein each correction dose during the offline operation includes calculating estimated glucose levels for immediately preceding offline sampling intervals using interpolation between a current isolated glucose measurement and a sample of glucose level from a most recent period of online operation.*

*24. The controller of claim 21, wherein the correction dose is calculated by the controller during the offline operation assuming a first target glucose level or range higher than a second target glucose level or range assumed during online operation.*

*25. The controller of claim 21, wherein the isolated glucose measurement is provided to the controller via a user interface used by the subject, and wherein each correction dosing operation includes use of one or more user interface functions selected from (i) the subject confirming that the correction dose is to be delivered, (ii) displaying a value of the correction dose to the subject, and (iii) accepting a modified value from the subject for use as the correction dose instead of the correction dose calculated by the controller.*

*26. The controller of claim 21, wherein online operation of the control algorithm further includes regular administration of correction doses of a counter-regulatory agent based on the control parameters of the control algorithm and the regular periodic sampling of glucose levels, and wherein the offline operation further includes counter-regulatory agent dosing operations each including administration of a dose of a counter-regulatory agent in response to a second isolated glucose measurement provided to the controller and calculated by the controller based on the second isolated glucose measurement, the control parameters, and the state of the control algorithm as evolved at the time of the counter-regulatory agent dosing operation.*

*27. The controller of claim 26, wherein the correction dose of insulin is calculated by the controller during periods when a counter-regulatory delivery channel or device is unavailable and assuming a first target glucose level or range higher than a second target glucose level or range assumed when the counter-regulatory delivery channel or device is available.*

*28. The controller of claim 21, wherein in both the online and offline operations, the control algorithm allows the subject to issue a microburst or rescue dose of counter-regulatory agent, a value of the microburst or rescue dose being calculated by the controller.*

*29. The controller of claim 21, wherein online operation of the control algorithm includes (v) administration of meal doses of insulin in response to a meal dose control input and automatically calculated by the controller based on preceding meal doses and corresponding prandial and post-prandial responses of the subject as reflected in the sampling of glucose levels via the glucose sensor and (vi) autonomously adjusting control parameters used to determine meal dose size to tailor the control parameters to the subject, and wherein offline operation including meal dosing operations each including administration of a meal dose of insulin in response to the meal dose control input and calculated by the controller based on the control parameters and the state of the control algorithm as evolved at the time of the meal dosing operation.*

*30. A method of operating a controller in a glucose level control system having a glucose sensor and an insulin delivery device, the controller having respective interfaces to the insulin delivery device and the glucose sensor (1) to convey an insulin dose control signal to the insulin delivery device for controlling infusion of insulin into a subject, and (2) to receive a glucose level signal from the glucose sensor indicating a glucose level of the subject, the method comprising:*

*performing online operation employing a control algorithm including (i) regularly administering correction doses of insulin based on control parameters of the control algorithm and regular periodic sampling of glucose levels of the subject via the glucose sensor, and (ii) autonomously adjusting the control parameters to tailor the control parameters to the subject; and*

*performing offline operation including (iii) evolving a state of the control algorithm over time without sampling of glucose levels and without automatic administration of the correction doses of insulin, and (iv) correction dosing operations each including administration of a correction dose of insulin in response to an isolated glucose measurement provided to the controller, the correction dose being calculated by the controller based on (i) the isolated glucose measurement, (ii) the control parameters, and (iii) the state of the control algorithm as evolved at the time of the correction dosing operation.*

*31. The method of claim 30, wherein the control algorithm employs regular periodic sampling intervals, and wherein evolving the control algorithm during the offline operation includes updating time effects of insulin previously administered to the subject.*

*32. The method of claim 31, wherein each correction dose during the offline operation includes calculating estimated glucose levels for immediately preceding offline sampling intervals using interpolation between a current isolated*

*glucose measurement and a sample of glucose level from a most recent period of online operation.*

*33. The method of claim 30, wherein the correction dose is calculated by the controller during the offline operation assuming a first target glucose level or range higher than a second target glucose level or range assumed during online operation.*

*34. The method of claim 30, wherein the isolated glucose measurement is provided to the controller via a user interface used by the subject, and wherein each correction dosing operation includes use of one or more user interface functions selected from (i) the subject confirming that the correction dose is to be delivered, (ii) displaying a value of the correction dose to the subject, and (iii) accepting a modified value from the subject for use as the correction dose instead of the correction dose calculated by the controller.*

*35. The method of claim 30, wherein online operation of the control algorithm further includes regular administration of correction doses of a counter-regulatory agent based on the control parameters of the control algorithm and the regular periodic sampling of glucose levels, and wherein the offline operation further includes counter-regulatory agent dosing operations each including administration of a correction dose of a counter-regulatory agent in response to a second isolated glucose measurement provided to the controller and calculated by the controller based on the second isolated glucose measurement, the control parameters, and the state of the control algorithm as evolved at the time of the counter-regulatory agent dosing operation.*

*36. The method of claim 35, wherein the correction dose of insulin is calculated by the controller during periods when a counter-regulatory delivery channel or device is unavailable and assuming a first target glucose level or range higher than a second target glucose level or range assumed when the counter-regulatory delivery channel or device is available.*

*37. The method of claim 30, wherein in both the online and offline operations, the control algorithm allows the subject to issue a microburst or rescue dose of counter-regulatory agent, a value of the microburst or rescue dose being calculated by the controller.*

*38. The method of claim 30, wherein online operation of the control algorithm includes (v) administration of meal doses of insulin in response to a meal dose control input and automatically calculated by the controller based on preceding meal doses and corresponding prandial and post-prandial responses of the subject as reflected in the sampling of glucose levels via the glucose sensor and (vi) autonomously adjusting control parameters used to determine meal dose size to tailor the control parameters to the subject, and wherein offline operation including meal dosing operations each including administration of a meal dose of insulin in response to the meal dose control input and calculated by the controller based on a second isolated glucose measurement, the control parameters, and the state of the control algorithm as evolved at the time of the meal dosing operation.*

*39. A controller for use in a glucose level control system having an insulin delivery device and a glucose sensor, the controller comprising:*

*processing circuitry including one or more processors;*

*memory; and*

*input/output circuitry,*

*the input/output circuitry providing respective interfaces to the insulin delivery device and the glucose sensor (1) to convey an insulin dose control signal to the insulin delivery device for controlling infusion of insulin into a subject, and (2) to receive a glucose level signal from the glucose sensor indicating a glucose level of the subject,*

*the memory storing computer program instructions executed by the processors to provide online operation and offline operation of the glucose level control system to generate the insulin dose control signal to achieve and maintain euglycemia in the subject, online operation employing a control algorithm including (i) administration of meal doses of insulin in response to a meal dose control input and automatically calculated by the controller based on preceding meal doses and corresponding prandial and post-prandial responses of the subject as reflected in sampling of glucose levels via the glucose sensor and (ii) autonomously adjusting control parameters used to determine meal dose size to tailor the control parameters to the subject, offline operation including (iii) evolving a state of the control algorithm over time without sampling of glucose levels, and (iv) meal dosing operations each including administration of a meal dose of insulin in response to the meal dose control input and calculated by the controller based on the control parameters and the state of the control algorithm as evolved at the time of the meal dosing operation.*

*40. The controller of claim 39, wherein online operation of the control algorithm further includes (i) regular administration of correction doses of insulin based on control parameters of the control algorithm and regular periodic sampling of glucose levels via the glucose sensor, and (ii) autonomously adjusting the control parameters to tailor the control parameters to the subject, and wherein the offline operation further includes (iii) evolving the state of the control algorithm over time without sampling of glucose levels and without automatic administration of the correction doses of insulin, and (iv) correction dosing operations each including administration of a correction dose of insulin in response to an isolated glucose measurement provided to the controller, the correction dose being calculated by the controller based on the isolated glucose measurement, the control parameters, and the state of the control algorithm as evolved at the time of the correction dosing operation.*

* * * * *